United States Patent [19]
Fleenor et al.

[11] Patent Number: 5,814,012
[45] Date of Patent: Sep. 29, 1998

[54] METHOD AND APPARATUS FOR RELIEVING EXCESS INSUFFLATION PRESSURE

[75] Inventors: Richard P. Fleenor, Englewood; Alan R. Lee, Littleton, both of Colo.

[73] Assignee: Birtcher Medical Systems, Inc., Utica, N.Y.

[21] Appl. No.: 30,632

[22] Filed: Mar. 12, 1993

Related U.S. Application Data

[63] Continuation of Ser. No. 251,736, Mar. 16, 1992, abandoned.

[51] Int. Cl.$^6$ .............. A61M 37/00; A61M 1/00; A61M 5/00; A61B 5/08
[52] U.S. Cl. .............. 604/26; 604/331; 604/118; 604/127; 604/128; 604/245; 604/256; 128/747; 128/748
[58] Field of Search .............. 128/747, 748; 604/26, 31, 118, 122, 128, 245, 256, 322–324

[56] References Cited

U.S. PATENT DOCUMENTS

| | | | |
|---|---|---|---|
| 2,579,113 | 12/1951 | Gardner. | |
| 3,414,011 | 12/1968 | Uddenberg | 137/510 |
| 3,730,168 | 5/1973 | McWhorter. | |
| 3,782,363 | 1/1974 | Davis. | |
| 3,889,707 | 6/1975 | Fay et al. | 137/251 |
| 3,982,533 | 9/1976 | Wiest. | |
| 4,207,887 | 6/1980 | Hiltebrandt et al.. | |
| 4,617,020 | 10/1986 | Kurtz | 604/321 |

FOREIGN PATENT DOCUMENTS

WO 89/04188   5/1989   WIPO.

*Primary Examiner*—John G. Weiss
*Assistant Examiner*—K. M. Reichle

[57] ABSTRACT

A method and apparatus for relieving insufflation pressure in a body cavity (18) in excess of a predetermined value are provided. A conduit assembly (24) extends from the body cavity (18) through the surface (61) of a fluid reservoir and has a port (63) positioned beneath the fluid surface (61). The relief pressure is selected by setting the relative positioning of the open end (63) and fluid surface (61). The apparatus avoids insufflation gas leakage problems associated with known insufflation pressure relief devices.

27 Claims, 3 Drawing Sheets

METHOD AND APPARATUS FOR RELIEVING EXCESS INSUFFLATION PRESSURE

CROSS-REFERENCE TO RELATED APPLICATION

The present application is a continuation-in-part of U.S. patent application Ser. No. 07/851,736, filed Mar. 16, 1992, now abandoned, which is incorporated herein by reference in its entirety.

FIELD OF THE INVENTION

This invention pertains to an improved apparatus for relieving insufflation pressure in excess of a predetermined value during surgical procedures wherein a body cavity is insufflated.

BACKGROUND OF THE INVENTION

Certain surgical procedures involve insufflation, i.e., introducing a gas such as certain inert gases or air into a body cavity. One such procedure is laparoscopic surgery. Laparoscopic surgery is a minimally invasive type of surgical procedure wherein surgical instruments and imaging equipment are inserted into a body cavity through an access cannula, thereby avoiding the need for large incisions. In such procedures, it is common to introduce a gas into the body cavity to separate a wall of the body cavity or other tissue from the surgical site. Sufficient clearance is thus provided to facilitate insertion and manipulation of the surgical instruments and viewing equipment.

It is important to monitor the introduction of the insufflation gas and the insufflation pressure in the body cavity during surgery. For example, a reduction in patient vital signs may result if the insufflation pressure is too high. It is thus desirable to maintain the insufflation pressure within a range where adequate insufflation is provided substantially without affecting the patient's vital signs. In addition, pressurized insufflation gas may spread from the surgical site into the patient's body resulting in post-surgery pain. Moreover, a high insufflation gas delivery rate can result in rapid depletion of the gas source, i.e., a gas canister, necessitating changing or replenishing of the source and prolonging surgery. For these and other reasons, it is useful to account for the insufflation gas and monitor the insufflation pressure.

Heretofore, the insufflation pressure has commonly been regulated by using a mechanical pressure relief valve which opens, thereby partially venting the body cavity, when the insufflation pressure reaches a predetermined limit. One such type of mechanical valve involves the use of a biasing device such as a spring to provide a back pressure such that the valve remains closed until the insufflation pressure is sufficient to overcome the back pressure. Thus, in theory, the insufflation pressure can be maintained below a desired limit in such devices by selecting an appropriate biasing device or device setting.

However, it has been found that such mechanical pressure relief valves may leak under normal operating conditions. It is often desired to maintain the insufflation pressure within a narrow pressure range during surgery. For example, during laparoscopic surgery, surgeons commonly insufflate the body cavity to approximately 14 mm Hg. However, it is generally desired to keep the insufflation pressure below about 16 mm Hg to avoid over-insufflation problems such as described above. Thus, pressure relief valves may be exposed to pressures near the selected relief pressure during surgery. Known mechanical pressure relief valves may leak as the insufflation pressure approaches the relief pressure and therefore fail to provide abrupt and positive pressure relief. As a result, the surgeon's ability to monitor the insufflation pressure and account for the insufflation gas may be impaired. In addition, the total amount of insufflation gas required during surgery may be increased due to the leakage. Moreover, because such mechanical pressure relief valves generally do not provide a visual indication when the relief pressure is exceeded, the surgeon may continue to introduce insufflation gas not knowing that the relief pressure has been exceeded, thereby possibly posing a risk to the patient and further increasing gas usage.

It is a further disadvantage of known mechanical pressure relief valves that such valves utilize moving parts which may malfunction or require maintenance. Moreover, some known mechanical pressure relief valves are of relatively complicated construction. Such valves thereby increase costs, particularly when used in disposable medical applications.

SUMMARY OF THE INVENTION

The present invention provides a method and apparatus for relieving insufflation pressure in a body cavity in excess of a predetermined value. The invention provides abrupt and positive pressure relief and reduces leakage problems associated with prior art devices. The invention also provides a visual indication when the relief pressure is exceeded, thereby increasing safety and reducing gas usage. In addition, an apparatus constructed in accordance with the present invention does not require moving parts thereby avoiding maintenance and reducing the likelihood of malfunction. Moreover, the present invention provides an apparatus which is of simple construction and may be produced inexpensively. The present invention therefore lends itself to disposable applications such that post use sterilization is unnecessary and contamination concerns are reduced.

According to one aspect of the present invention, an apparatus for relieving insufflation pressure in a body cavity in excess of a predetermined value is provided. The apparatus comprises a receptacle containing a fluid and an insufflation gas exhaust assembly. The exhaust assembly extends into the fluid contained in the receptacle and has a first end positioned a predetermined distance beneath the top surface of the fluid contained in the receptacle such that insufflation gas is exhausted from the body cavity via the first end of the exhaust assembly when the insufflation pressure exceeds the predetermined value. That is, the fluid exerts a back pressure on the exhaust assembly such that insufflation gas does not flow through the port unless the insufflation pressure exceeds the back pressure. Thus, the relief pressure can be selected by setting the predetermined distance between the top surface of the fluid in the receptacle and the first end of the exhaust assembly, e.g., by changing the fluid level in the receptacle or by moving the first end relative to the top surface of the fluid. The exhaust assembly can comprise a tube which is adapted for interconnection to an exhaust port from the body cavity. The exhaust assembly preferably includes a conduit which is fixed with respect to the receptacle such that the predetermined distance is set by adding or subtracting fluid from the receptacle. The receptacle can comprise a bag or other rigid or non-rigid container. Preferably, the receptacle is at least partly transparent, i.e., the receptacle is wholly or partially comprised of transparent or translucent material. Additionally, the receptacle is preferably formed from inexpensive materials, such as certain plastic materials, as it is desirable to dispose of the receptacle after use. Calibration markings may be provided on the receptacle to assist in setting the fluid level. The fluid surface can be exposed to the ambient atmosphere. The fluid should be a sterile solution such as sterile saline solution.

According to another aspect of the present invention, an insufflation system is provided. The system comprises an insufflation gas source, an inlet assembly for one-way delivery of gas from the gas source to a body cavity, and an outlet assembly for one-way venting of insufflation gas from the body cavity. The outlet assembly extends from the body cavity into a fluid contained in a receptacle and includes a first end submerged a predetermined distance beneath the surface of the fluid contained in the receptacle. The fluid may comprise a sterile fluid such as sterile saline solution.

According to a further aspect of the present invention, a method for relieving excess insufflation pressure in a body cavity is provided. The method includes the steps of providing an insufflation gas exhaust assembly including a receptacle containing a fluid and an exhaust line extending from a body cavity into the fluid, and establishing one-way insufflation gas communication from the body cavity to the receptacle via the exhaust line. The step of establishing can be accomplished by pressurizing the body cavity such that insufflation gas flows therefrom and/or opening a valve or cover to allow flow through the conduit assembly.

According to a still further aspect of the present invention, a method for venting a body cavity is provided. The method comprises the steps of setting the relative positioning between a first end of an exhaust line extending from a body cavity and the top surface of a fluid contained in a receptacle so that the first end is positioned a preselected distance beneath the surface and establishing one-way insufflation gas communication from the body cavity to the receptacle via the exhaust line. Insufflation gas thus flows from the body cavity to the first end of the exhaust line when the insufflation pressure exceeds a predetermined value. The relative positioning between the first end and the fluid surface can be selected by changing the fluid level in a receptacle or by moving the first end of the exhaust line. The method can further include the step of flowing insufflation gas from a gas source to the body cavity.

BRIEF DESCRIPTION OF THE DRAWINGS

For a more complete understanding of the present invention and for further advantages thereof, reference is now made to the following detailed description taken in conjunction with the accompanying drawings, in which.

DETAILED DESCRIPTION OF THE INVENTION

Figure 1:
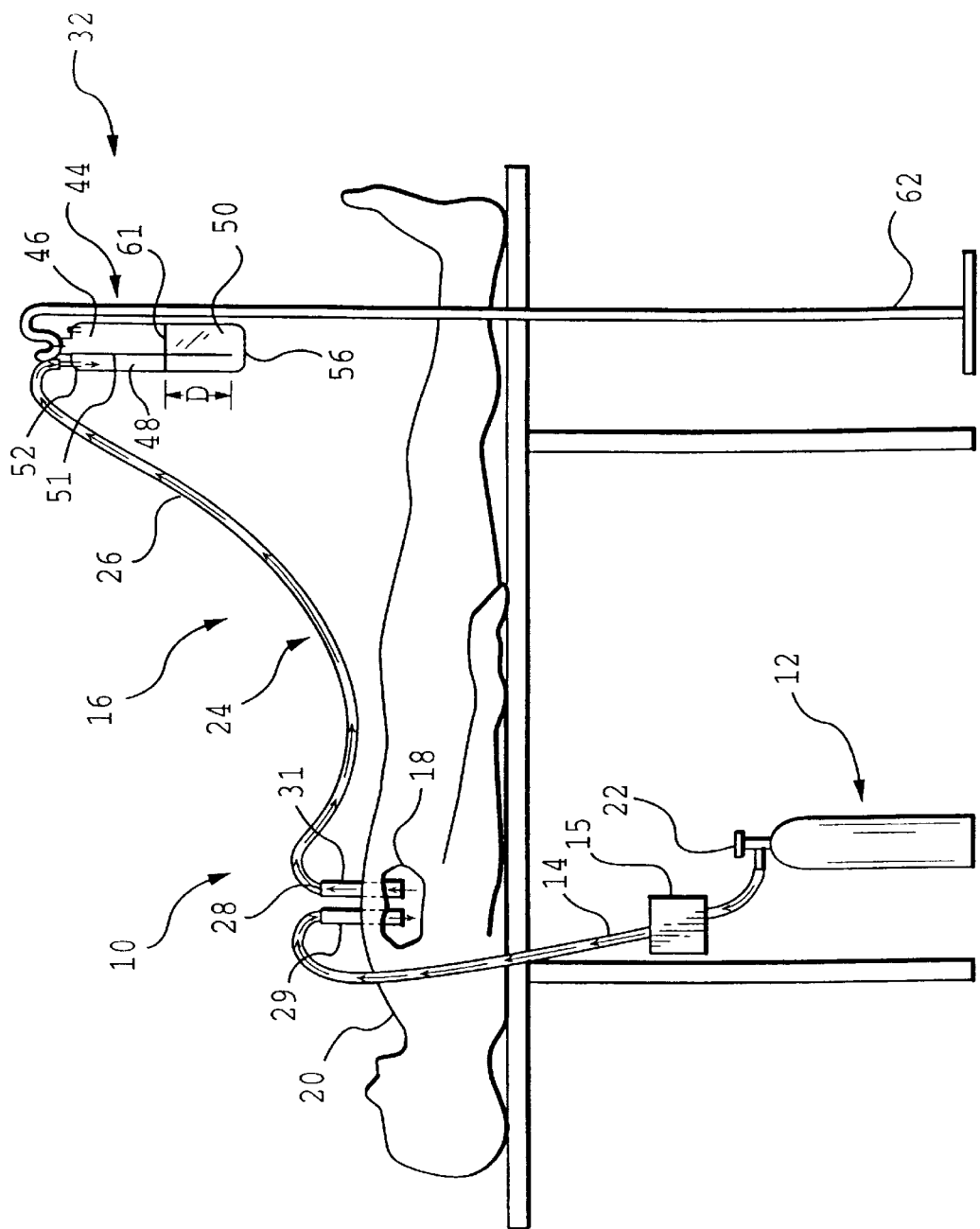
FIG. 1 is a front view of an insufflation system constructed in accordance with an embodiment of the present invention.

Referring to FIG. 1, an insufflation system constructed in accordance with the present invention is generally identified by the reference numeral 10. The system 10 comprises an insufflation gas source 12, a gas delivery conduit assembly 14, and a pressure relief assembly 16. A control unit 15 for controlling gas flow from the gas source 12 may be included within gas delivery conduit assembly 14.

The system 10 can be used in connection with any insufflation application wherein it is desired to relieve insufflation pressure in excess of a preselected value. In the illustrated embodiment, the system 10 is depicted in a typical laparoscopic surgery setting. In such a setting, for example, a body cavity, generally identified by the reference numeral 18, of a patient 20 may be insufflated to provide clearance between the surgical site and the abdominal wall or other surrounding tissue, thereby facilitating manipulation of surgical tools and viewing equipment.

An insufflation gas is delivered from the gas source 12 to the body cavity 18 through the gas delivery assembly 14. The gas source 12 can be a canister of a known insufflation gas, such as $CO_2$, and can be incorporated into a gas cart (not shown) or provided separately. A valve 22 is provided to regulate the flow of gas from the gas source 12. The gas source 12 and/or control unit 15 can further include a gas flow or pressure meter and/or a gauge to monitor the remaining gas supply.

The gas delivery assembly 14 sealably engages an outlet of the gas source 12 and extends into the body cavity 18 to deliver the insufflation gas thereto. Only one-way gas flow should be permitted through the gas delivery assembly 14 to avoid contamination of the gas source 12 or upstream components. The assembly 14 may comprise a single gas line or a series of gas lines. For example, the insufflation gas may be delivered to the body cavity 18 through a cannula which can also be used to provide access to the surgical site for surgical tools, viewing equipment and the like, thereby reducing the required number of incisions. Thus, the insufflation gas may be routed to the body cavity 18 through a gas line from the source 12, internal passageways of a surgical instrument, and a cannula. Alternatively, a separate conduit assembly dedicated to delivery of the insufflation gas may be provided, and the gas source 12 may be interconnected to an inlet port of an access cannula 29, as shown.

A pressure relief assembly 16 is provided to relieve insufflation pressure in the body cavity 18 in excess of a predetermined value. The assembly 16 comprises a gas outlet conduit subassembly 24 extending from the body cavity 18 and a fluid reservoir subassembly 32 for selectively relieving excess insufflation pressure. The gas outlet subassembly 24 may comprise a series of gas lines for selectively delivering insufflation gas from the body cavity 18 to the fluid reservoir subassembly 32, or the gas outlet subassembly 24 may be provided by way of a single tube. In the illustrated embodiment, the gas outlet subassembly 24 comprises a length of flexible tubing 26 which sealably engages an exhaust port 28 of the access cannula 31. The tubing 26 should have a width sufficient to accommodate flow of insufflation fluid therethrough with little resistance. For example, the tubing 26 can have an inside diameter of about ¼–3/16 inch. The tubing 26 can be sealably attached to the cannula 31 by way of a standard "LUER" lock, frictional engagement, or other means. If desired, a valve or cover can be included in the gas outlet subassembly 24 to selectively close fluid communication between the body cavity 18 and the reservoir subassembly 32.

Generally, the reservoir subassembly 32, which will be described in greater detail below, comprises a fluid reservoir and an insufflation fluid passageway separated from the reservoir by a substantially fluid impermeable barrier. The insufflation fluid passageway extends through the reservoir fluid surface and has an open end a predetermined distance beneath the surface. It will thus be appreciated that the reservoir fluid will fill the insufflation fluid passageway to the level of the surface of the reservoir if the pressure in the insufflation fluid passageway is equal to the pressure exerted on the surface of the reservoir. If the pressure in the insufflation fluid passageway is greater than the pressure on the surface of the reservoir, the level of reservoir fluid in the insufflation fluid passageway will be reduced accordingly. Thus, because insufflation pressure is communicated from the body cavity 18 to the insufflation fluid passageway, insufflation fluid can pass from the body cavity 18, through the open end of the insufflation fluid passageway, and to the surface of the reservoir when the insufflation pressure is sufficiently greater than the pressure on the surface of the reservoir. At the surface, the insufflation fluid may be vented to the ambient atmosphere or the fluid may be collected and/or filtered.

The parameters involved in determining the relief pressure of the pressure relief assembly thus include the density of the reservoir fluid, the pressure exerted on the surface of the reservoir and the distance between the reservoir surface and the open end of the insufflation fluid passageway. It will therefore be appreciated that many configurations of the reservoir subassembly 32 are possible. For example, the reservoir subassembly 32 can comprise a bottle, beaker, bag or other receptacle and the reservoir surface can be exposed to the ambient atmosphere or to non-atmospheric pressure. A flexible bag or other inexpensive, easily disposed receptacle is preferred as it is desirable to dispose of the receptacle after use to avoid sterilization costs and attendant risks. The insufflation fluid passageway can be an integral portion of a receptacle or may be provided by way of a conduit which is moveable relative to such a receptacle. The distance between the reservoir surface and the open end of the insufflation fluid passageway can therefore be adjusted by changing the reservoir fluid level or by moving such a moveable conduit relative to the receptacle.

As shown, separate cannulas 29 and 31 are provided to allow separate access to the body cavity 18 for assemblies 14 and 16 and to allow for one-way insufflation gas flow throughout the system 10. This construction provides a number of advantages. First, since the pressure relief assembly 16 does not communicate with the gas delivery assembly 14 (other than via body cavity 18), accurate regulation of the insufflation pressure in the body cavity 18 is insured. It has been found that systems which attempt to regulate the insufflation pressure in a body cavity by monitoring pressure in an insufflation gas delivery line can be inaccurate due to differences between the pressure inside the body cavity and in the delivery line. Such differences result at least in part from back pressure reflected from the inlet port to the body cavity which is normally somewhat restricted. The present invention avoids this problem by positioning the reservoir subassembly 32 downstream from the body cavity 18 in a one-way flow system 10. The illustrated construction also lends itself to disposable, add-on applications. That is, the pressure relief assembly 16 or portions thereof can be provided separately and disposed of after use. Other advantages will be apparent to those skilled in the art.

Figure 2:
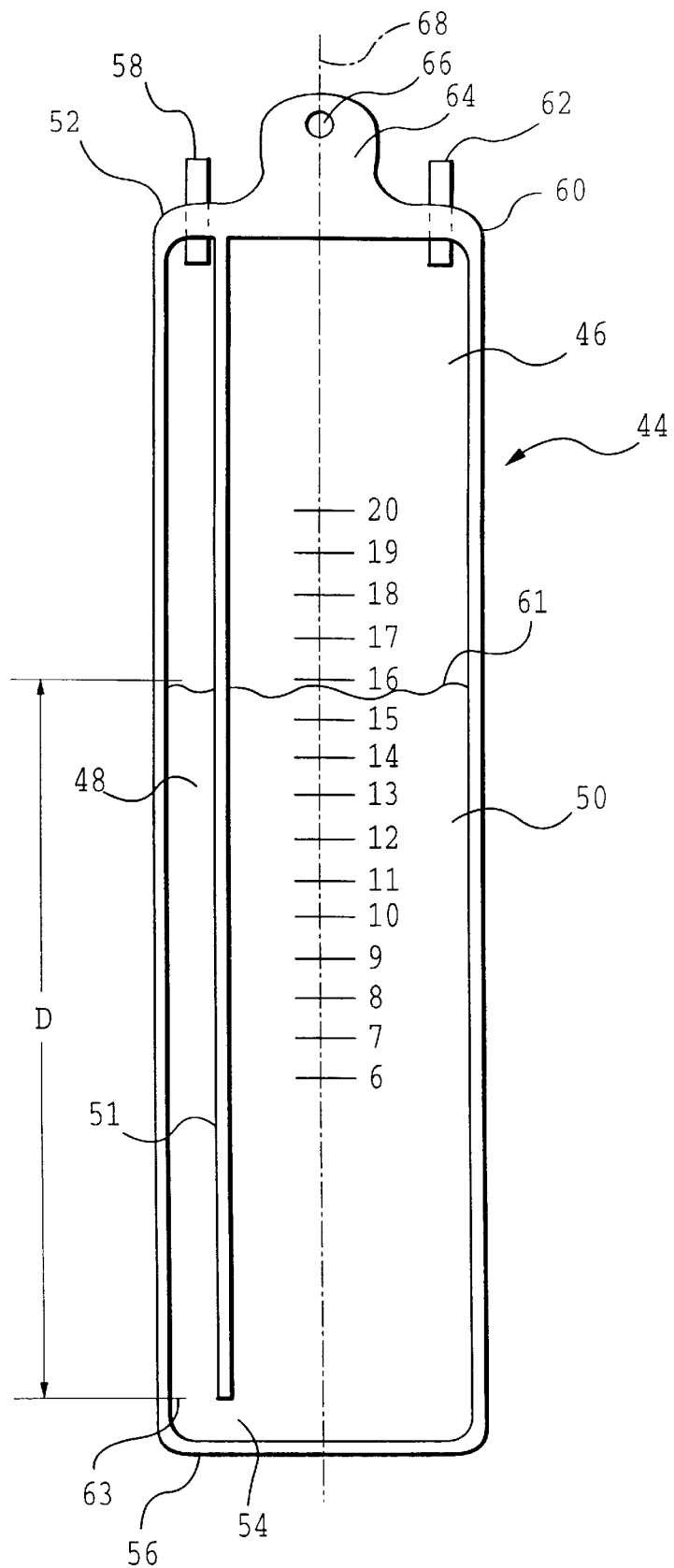
FIG. 2 is a front view of a receptacle which can be used in the system of FIG. 1.

In the embodiment of FIGS. 1 and 2, the reservoir subassembly 32 comprises a receptacle 44 such as a bag formed from flexible elastomeric material. Preferably, the receptacle 44 is at least partly transparent to allow viewing into the receptacle 44. The receptacle 44 can conveniently be constructed by attaching two thin sheets together at portions thereof, e.g. by heat sealing, RF bonding, adhesive bonding or other technique, to form an internal fluid retaining space 46. The illustrated receptacle 44 includes an insufflation gas conduit portion 48 and a reservoir portion 50 wherein the portions 48 and 50 are separated by a substantially fluid impermeable barrier 51. The barrier 51, which can be formed by sealing the front and back walls of the receptacle 44 together, extends downwardly from a top edge 52 of the receptacle 44. A gap 54 is provided in the barrier 51 or between the barrier 42 and a bottom wall 56 of the receptacle 44 to allow fluid communication between the portions 48 and 50. Preferably, the gas conduit portion 48 has relatively small volume as compared to the reservoir portion 50 such that a change in fluid level in the gas conduit 48 results in a smaller change in the fluid level in the reservoir portion 50.

Insufflation gas is introduced into the conduit portion 48 through adapter tube 58. The adapter tube 58, which is sealably disposed within a peripheral seal 60 of the receptacle 44 above the fluid surface 61, is adapted to sealably engage tubing 26 from the body cavity 18 of the patient 20. The adapter tube 58 and the tubing 26 may be interconnected by way of a locking assembly such as a "LUER" lock, frictional engagement or other means. In the illustrated embodiment, the adapter tube 58 and tubing 26 are friction fitted so that a seal is formed between the adapter tube 58 and tubing 26 when they are mated. The illustrated receptacle 44 also includes a second tube 62 which extends through the peripheral seal 60 above the fluid surface 61 into the reservoir portion 50 of the receptacle 44. The tube 62 allows venting of the insufflation gas and can be used to add fluid to the receptacle 44.

The receptacle 44 may be adapted to be hung out of the way during surgery, thereby conserving operating theater space and reducing the likelihood of tilting or spilling of the receptacle 44 or its contents. As illustrated, the receptacle 44 is provided with a bulge 64 including a sealed opening 66 for this purpose. The receptacle 44 can thus be hung from an IV or plasma bag stand 65 or other hanger assembly. Preferably, the opening 66 is positioned at or near a longitudinal axis 68 of the receptacle 44 so that the axis 68 tends to orient vertically when fluid is added to the receptacle 44.

As shown in FIG. 2, markings can be provided on the receptacle 44 for use in setting the desired relief pressure. Because the relief pressure is proportional to the distance D between the open end or port 63 of the insufflation gas conduit portion 48 and the surface 61 of the reservoir fluid, the relief pressure can be set at a desired level by filling the receptacle 44 with the fluid until the fluid reaches the appropriate level. Various fluid levels and/or associated relief pressure settings can thus be conveniently calibrated by placing markings directly on the receptacle 44. Calibration can be accomplished experimentally or by using known formulas, e.g., relating 1 mm Hg to a depth of the reservoir fluid. It will be appreciated that many different reservoir fluids can be used in accordance with the present invention. However, the reservoir fluid should be a sterile fluid such as 7% sterile saline solution to reduce the likelihood of contamination in the event that the fluid enters the body cavity 18.

Figure 3:
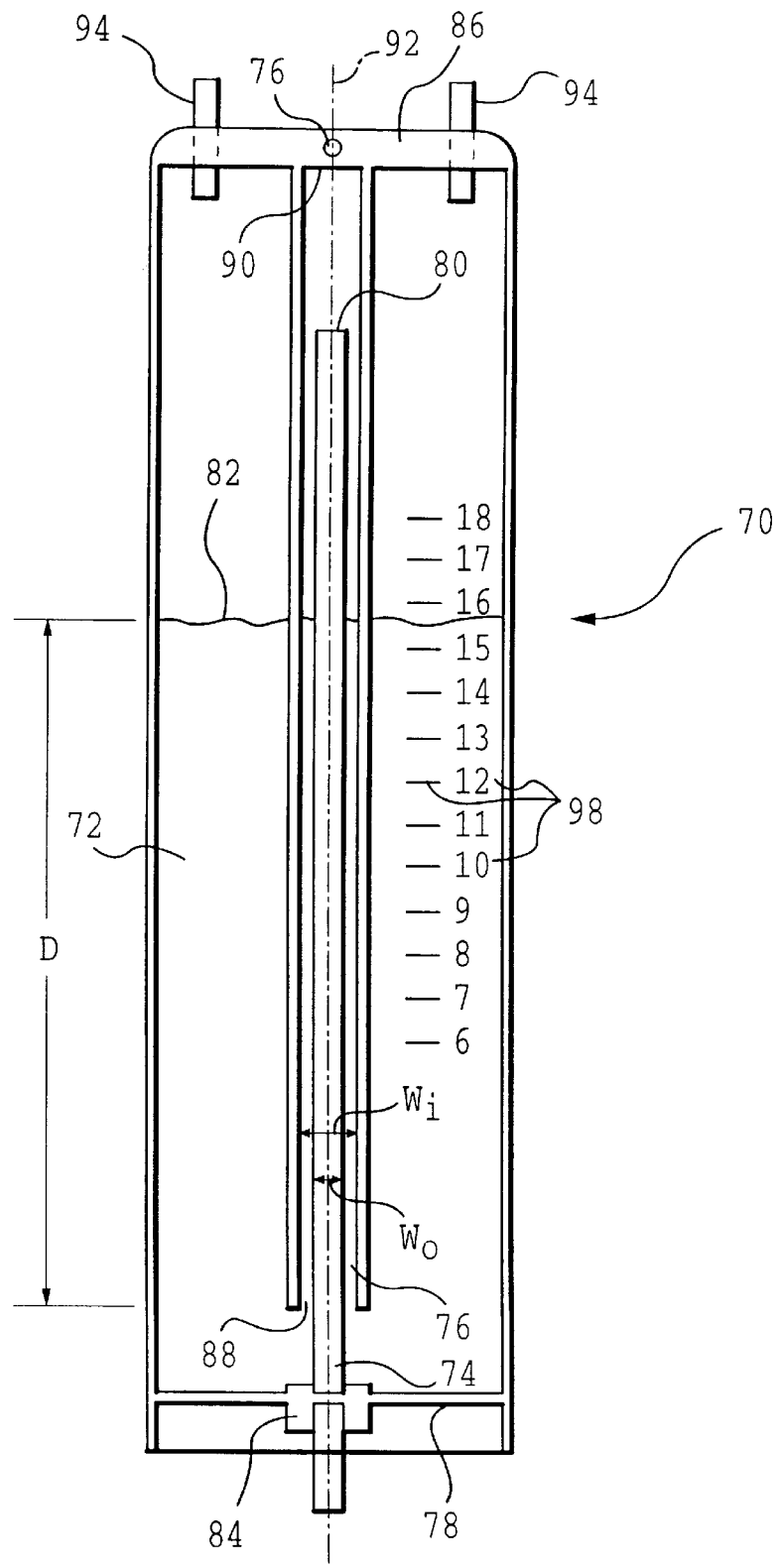
FIG. 3 is a front view of another receptacle constructed in accordance with the present invention.

Referring to FIG. 3, a front view of a receptacle 70 constructed in accordance with an alternative embodiment of the present invention is shown. The receptacle 70 can comprise a bottle, beaker, bag or other container. Preferably, the receptacle 70 is at least partly transparent to allow viewing of the reservoir fluid 72 therein and to allow viewing of bubbles rising through the fluid 72 when the predetermined relief pressure is exceeded. In the illustrated embodiment, the receptacle 70 is formed from two sheets of clear plastic which are sealed together at peripheral portions thereof to define an internal fluid retaining space. For ease of construction, the illustrated receptacle 70 is formed from sheet materials which can be sealably attached together by heat sealing or RF welding. Alternatively, the sheets could be attached together by an adhesive or other means.

Insufflation fluid from a body cavity is introduced into the receptacle 70 by way of a conduit assembly including a tube 74 and a channel 76. The tube 74, which is in fluid communication with the body cavity, extends through a bottom edge 78 of the receptacle 70 and has an open end 80 within the channel 76. A seal 84 is provided in the bottom edge 78 about the tube 74 to substantially prevent leakage of reservoir fluid 72. Any suitable means may be utilized to provide the seal 84. In the illustrated embodiment, the seal 84 comprises a widened portion wherein the sheet materials of the receptacle are heat sealed or RF welded together. Preferably, the open end 80 is positioned above the surface 82 of the reservoir fluid 72 to reduce the likelihood that fluid 72 will flow through the tube 74 to the body cavity.

The channel 76 extends downwardly from a top edge 86 of the receptacle 70 and has a port 88 positioned a predetermined distance D beneath the surface 82. The channel 76 has an inside width $W_i$ greater than an outside width $W_o$ of the tube 74 such that insufflation fluid can flow therebetween. It will be appreciated that the channel 76 is sealed at an upper edge 90 so that insufflation fluid flowing from the body cavity can only escape from the conduit assembly through port 88. In this regard, the channel 76 may comprise, for example, a tube having a sealed upper end. In the illustrated embodiment, the channel 76 is formed by sealing portions of the sheet materials of the receptacle 70 together, e.g., by heat sealing or RF bonding. Preferably, the channel 76 is positioned along a vertical centerline 92 of the receptacle 70 to reduce horizontal movement of the center of gravity and tilting of the receptacle 70 due to flow of reservoir fluid 72 into or out of the channel 76. The illustrated configuration has also been found to reduce or eliminate the incidence of undesired clinging of the opposing sheet materials of the receptacle 70, which clinging could obstruct the flow of insufflation fluid.

The receptacle 70 further includes at least one opening through a wall of the receptacle 70 above the surface 82 to allow introduction of reservoir fluid 72 to the receptacle 70 and escape of insufflation fluid therefrom. In the illustrated embodiment, wherein the channel 76 is provided by sealing the sheet materials of the receptacle 70 together such that insufflation fluid cannot flow around the channel 76 above the surface 82, openings are provided in the receptacle 70 on both sides of the channel 76. As shown, the openings comprise tubes 94 sealably extending through the top edge 86 of the receptacle 70. The illustrated receptacle also includes a hole 96 positioned on or near the centerline 92 to allow the receptacle to be hung from an IV stand or other hanger, thereby conserving space in the operating theater. In addition, the illustrated receptacle includes markings 98 on a surface thereof to aid in setting the reservoir fluid level.

In operation, an insufflation system constructed in accordance with an embodiment of the present invention can be used as follows. Operating room personnel can first remove a disposable bag and tubing from protective packaging using aseptic techniques. The bag and connected tubing can then be passed outside of a sterile field, retaining a free end of the tubing in the sterile field. The bag can be hung on an IV stand or other hanger and filled with sterile saline solution to the desired relief pressure as indicated by markings on the bag. The free end of the tubing can then be connected to the vent port of a cannula extending from a body cavity of a patient. Insufflation fluid is delivered from a source to the body cavity, e.g., by opening valves, to provide the desired insufflation pressure. When in use, bubbles will be seen rising through the reservoir fluid whenever the set relief pressure is exceeded. After use, the tubing should be detached from the cannula, or fluid communication between the bag and cannula should otherwise be closed, prior to removing the cannula from the patient. The bag and tubing, which are of simple construction, can be discarded after use in accordance with accepted medical procedures.

The present invention has a number of advantages over known insufflation systems. The present invention provides an insufflation system capable of abrupt and positive pressure relief. An apparatus constructed and used in accordance with the present invention can thus function near the selected relief pressure substantially without leakage of the insufflation gas. A physician's ability to monitor the insufflation pressure and account for the insufflation gas is therefore enhanced. In addition, the likelihood of depleting the insufflation gas source during surgery is reduced thereby avoiding time consuming interruptions during surgery. The present invention also provides a visual indication, i.e., bubbles, when the relief pressure is exceeded. Moreover, the present invention provides a pressure relief apparatus of simple construction which lends itself to disposable applications. The present invention also provides a pressure relief apparatus which can be constructed without moving parts which may malfunction or require maintenance. Additional advantages of the present invention will be apparent to those skilled in the art.

While the present invention has been described in relation to specific embodiments thereof, additional alternative embodiments apparent to those skilled in the art in view of the present disclosure are intended to fall within the scope of the present invention as further defined by the claims set forth below.

What is claimed:

1. An apparatus for use in an insufflation system to relieve insufflation pressure in a body cavity in excess of a predetermined value, said insufflation system including a source of insufflation gas, an inlet conduit for one-way insufflation gas flow from said source to said body cavity, and an exhaust port for one-way insufflation gas flow away from said body cavity, said apparatus comprising:

a receptacle containing a fluid; and conduit means for allowing one-way flow of insufflation gas from said body cavity into said fluid contained in said receptacle when an insufflation pressure in said body cavity exceeds a predetermined value, said conduit means having a first end for receiving insufflation fluid from said body cavity via said exhaust port and a second end positioned a predetermined distance beneath a top surface of said fluid contained in said receptacle wherein, during use, insufflation gas is exhausted from said body cavity via said conduit means when said insufflation pressure exceeds said predetermined value.

2. The apparatus of claim 1, wherein said receptacle has an opening therein above said top surface of said fluid contained in said receptacle for passage of an insufflation gas.

3. The apparatus of claim 1, wherein said receptacle comprises a flexible bag.

4. The apparatus of claim 3, wherein said bag is adapted to be hung above said body cavity from a hanger assembly.

5. The apparatus of claim 1, wherein said receptacle is at least partly transparent.

6. The apparatus of claim 1, further comprising means for setting said predetermined distance between said top surface and said second end.

7. The apparatus of claim 6, wherein said means for setting comprises means for adjusting a level of said top surface.

8. The apparatus of claim 6, wherein said means for setting comprises an opening for adding fluid to said receptacle or for subtracting fluid therefrom.

9. The apparatus of claim 1, wherein said conduit means comprises a first conduit extending from a point above said top surface of said fluid contained in said receptacle to said second end.

10. The apparatus of claim 9, wherein said conduit means further comprises a second conduit extending upwardly from a bottom edge of said receptacle and having an open end positioned within said first conduit, wherein said second conduit has a width less than a width of the first conduit.

11. The apparatus of claim 9, wherein said first conduit comprises a compartment of said receptacle formed by sealing a portion of a front wall of said receptacle to a portion of a back wall thereof.

12. The apparatus of claim 9, wherein said first conduit is positioned substantially along a vertical centerline of said receptacle.

13. The apparatus of claim 1, wherein said receptacle comprises a first compartment and a second compartment, the compartments separated by a substantially fluid impermeable partition, communication between said first and second compartments provided by a passageway located a predetermined distance D beneath said top surface of said fluid contained in said receptacle, wherein the distance D is selected such that insufflation gas passes through said passageway when said insufflation pressure exceeds said predetermined value.

14. The apparatus of claim 1, wherein said receptacle includes calibration markings to assist in setting a level of said top surface of said fluid contained in said receptacle.

15. The apparatus of claim 1, wherein said receptacle contains a substantially sterile fluid.

16. An insufflation system, comprising:
    a source of insufflation gas;
    inlet means, extending from said source to a body cavity, for one-way delivery of said gas to the body cavity;
    a receptacle containing a fluid; and
    outlet means, separate from said inlet means, extending from said body cavity to said receptacle, for one-way venting of insufflation gas from said body cavity into said receptacle when the pressure in said body cavity exceeds a predetermined value, said outlet means including a first end submerged a predetermined distance beneath a surface of said fluid contained in said receptacle.

17. The system of claim 16, wherein said receptacle contains sterile saline solution.

18. A method for relieving excess insufflation pressure in a body cavity, comprising the steps of:
    providing an insufflation gas exhaust assembly including a receptacle for containing a fluid and an exhaust line having a first open end and a second end for submersion within said fluid;
    attaching said first open end to an exhaust port for exhausting insufflation gas from said body cavity; and
    establishing one-way insufflation fluid communication from said body cavity to said receptacle via said exhaust line.

19. The method of claim 18, wherein said step of establishing comprises pressurizing the body cavity such that insufflation fluid flows therefrom.

20. The method of claim 18, wherein said step of establishing comprises opening a valve to allow flow of insufflation fluid through said exhaust line.

21. A method for venting insufflation gas from a body cavity comprising the steps of:
    setting the relative positioning between a first end of an exhaust line extending from a body cavity and the top surface of a fluid contained in a receptacle so that the first end is positioned a preselected distance beneath the surface; and
    connecting a second end of said exhaust line to an exhaust port for exhausting insufflation gas from said body cavity so as to establish one-way insufflation gas communication from said body cavity to said receptacle via said exhaust line.

22. The method of claim 21, further comprising the step of:
    flowing insufflation gas from a gas source to said body cavity.

23. The method of claim 21, wherein said step of setting comprises adding fluid to said receptacle.

24. An apparatus for relieving insufflation pressure in a body cavity in excess of a predetermined value, comprising:
    a fluid receptacle formed from flexible film material for containing a predetermined level of fluid; and
    conduit means for providing one-way insufflation gas communication from a body cavity to said fluid receptacle having a first end disposed at a predetermined position within said fluid receptacle and a second end detachably connectable to an exhaust port from the body cavity for receiving insufflation gas from said body cavity via said exhaust port wherein, during use, the first end is submerged within a predetermined level of fluid contained in said fluid receptacle and insufflation gas is permitted to pass from the body cavity through the conduit means and into said fluid receptacle when pressure in the body cavity exceeds a predetermined value.

25. The apparatus of claim 24, wherein said fluid receptacle comprises a flexible bag.

26. The apparatus of claim 24, wherein said conduit means comprises a compartment of said fluid receptacle formed by sealing a portion of a front wall of said fluid receptacle to a portion of a backwall thereof.

27. The apparatus of claim 24, wherein said conduit means comprises flexible film material.

* * * * *